July 4, 1972 S. D. McGREDY IV Plant Pat. 3,226
ROSE PLANT
Filed Oct. 8, 1970
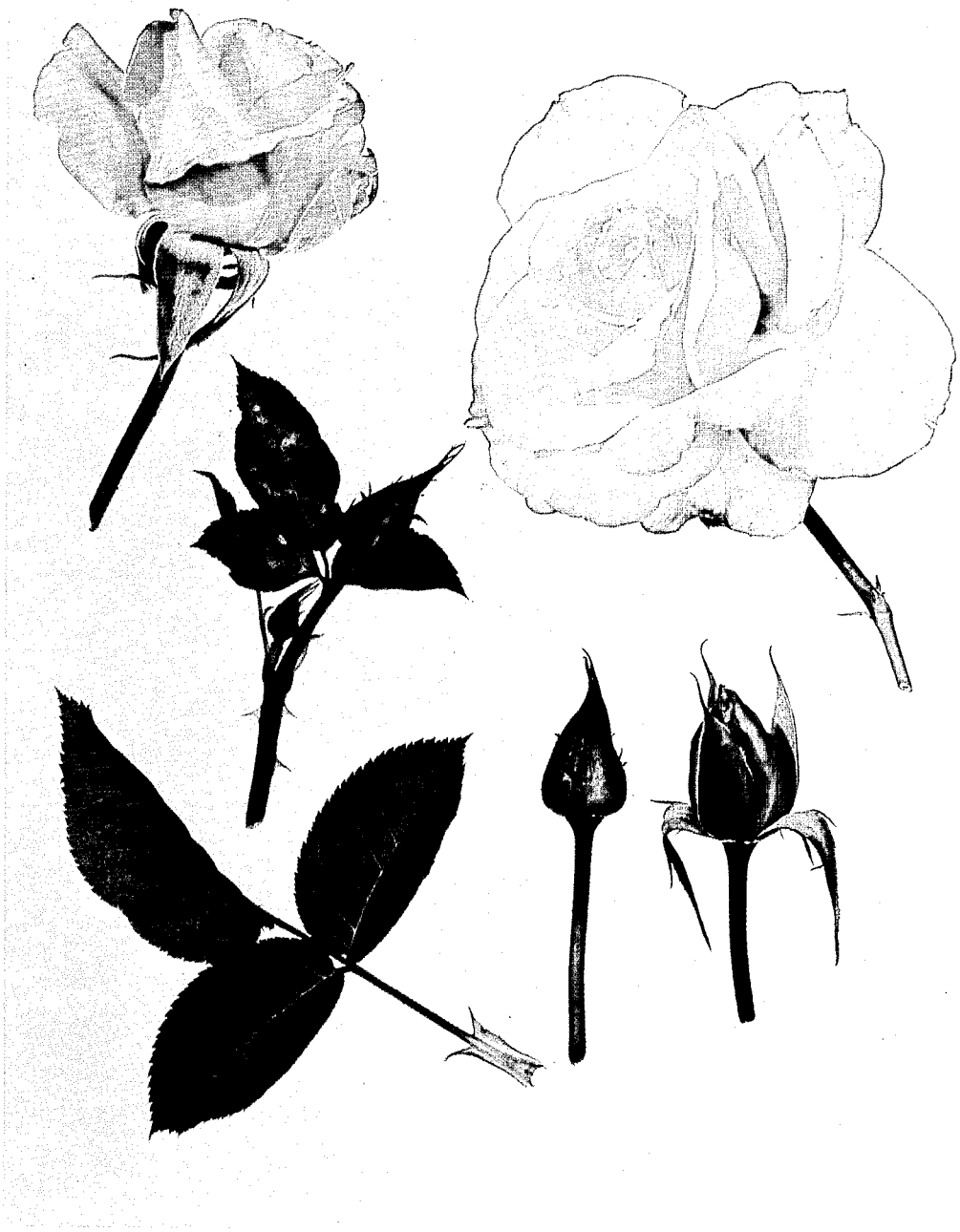

United States Patent Office

Plant Pat. 3,226

Patented July 4, 1972

3,226

ROSE PLANT

Samuel D. McGredy IV, Portadown, Ireland, assignor to Howard Rose Company, Hemet, Calif.

Filed Oct. 8, 1970, Ser. No. 79,365

Int. Cl. A01h 5/00

U.S. Cl. Plt.—11 1 Claim

The present invention relates to a new and distinct variety of rose plant of the hybrid tea class, which was originated by me by crossing the rose variety known as "Paddy McGredy" (U.S. Plant Pat. No. 2,327) with the rose variety known as "Prima Ballerina" (unpatented), the former being the seed parent and the latter being the pollen parent.

As the result of this breeding, I have produced a new and improved rose variety which is distinguished from its parents, as well as from all other rose varieties of which I am aware, as evidenced by the following unique combination of characteristics which are outstanding in the new variety:

(1) A bushy, upright and vigorous habit of growth;
(2) Abundant and attractive foliage;
(3) A profuse blooming habit, both outdoors and in the greenhouse;
(4) High-centered flowers of double form and large size; and
(5) A distinctive and attractive light red flower color.

Asexual reproduction of my new variety by budding, as performed by me in Ireland and performed on my behalf at Hemet, Calif., U.S.A., shows that the foregoing characteristics come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new rose variety, with color terminology in accordance with the Royal Horticultural Colour Chart, published by the Royal Horticultural Society of London, except where general color terms of ordinary dictionary significance are obvious:

Type: Hardy; bush; greenhouse; seedling; for cut flowers and for garden decoration.
Class: Hybrid tea.
Breeding: Seedling.
*Seed parent.*—"Paddy McGredy."
*Pollen parent.*—"Prima Ballerina."
Propagation: Holds its distinguishing characteristics through succeeding propagations by budding.

*Flowers*

Locality where grown and observed: Hemet, Calif., U.S.A.
Flowers Borne: Sometimes singly, but usually 3 or 4 to the stem; in irregular clusters; on normal stems of medium to long length.
Quantity of bloom: Very free, both outdoors and in the green-house.
Continuity: Nearly continuous during the growing season.
Fragrance: Slight. Nature—spicy.
Bud:
*Peduncle.*—Average length; average caliper; erect; almost smooth; some gland-tipped cilia; few prickles. Color—Near Yellow-Green, Group 146B.
*Before calyx breaks.*—Size—medium. Form—medium length; globular; with a conspicuous neck; with foliaceous appendages and few gland-tipped cilia on the surface of the bud; usually with slender, bristle-like foliaceous parts extending beyond the tip of the bud equal to ¼ or more of its length.
*As calix breaks.*—Color—Near Red-Purple, Group 59B.
*Sepals.*—Inner surface—with fine, wooly tomentum. Margins—most have foliaceous appendages lined with gland-tipped cilia and hairs.
*As first petal opens.*—Size—average. Form—medium length; globular; some high-centered. Color—outside—Near Red, Group 53D, with very small base of near Yellow, Group 8A. Inside—Near Red, Group 52A, with very small base of near Yellow, Group 8A.
*Opening.*—Opens up well; is not retarded from opening by cold, hot, wet or dry weather.

Bloom:
*Size (when fully open).*—Average; from 4½ inches to 5½ inches.
*Petalage.*—Double; from 30 to 35 petals, plus 4 or 5 petaloids; arranged irregularly.
*Form.*—High-centered and globular at first, but becoming open to high-centered globular; petals at first being somewhat tightly cupped, with tips rolled outward, but later becoming somewhat loosely cupped, with tips rolled outward at maturity.
Petals:
*Texture.*—Medium thick; moderately soft.
*Appearance.*—Inside — slightly shiny. Outside — slightly shiny.
*Shape.*—Outside—oval, with apex flat. Intermediate—oval, with apex rounded. Inside—nearly oval, with apex rounded.

This description of a newly opened flower was made from a rose grown outdoors during the month of August at Hemet, Calif., U.S.A.:

*Color.—Outer petal*—outside surface—Near Red-Purple, Group 58B, with very small base of near Yellow, Group 8A, and shading somewhat lighter toward outer edges of petals; inside surface—Near Red-Purple, Group 58B, with very small base or near Yellow, Group 8A, and shading somewhat lighter toward outer edges of petals.
*Intermediate petal*—outside surface—Near Red-Purple, Group 58B, with very small base of near Yellow, Group 8A, and shading somewhat lighter toward outer edges of petals, inside surface—Near Red-Purple, Group 58C, with very small base of Yellow, Group 8A, and shading somewhat lighter toward outer edges of petals; inside surface—Near surface—Near Red-Purple, Group 58B, with very small base of near Yellow, Group 8A, and shading somewhat lighter toward outer edges of petals; inside surface—Near Red-Purple, Group 58C, with very small base of near Yellow, Group 8A, and shading somewhat lighter toward outer edges of petals.

This description was made from a rose that was open for three days outdoors during the month of August at Hemet, Calif., U.S.A.:

*Color.—Outer petal*—outside surface—Near Red-Purple, Group 58B, with very small base of near Yellow, Group 8C and shading to light pink toward outer edges of petals; inside surface—Near Red-Purple, Group 58C, with very small base of near Yellow, Group 8C and shading to light pink toward outer edges of petals. *Inner petal*—outside surface—Near Red-Purple, Group 58B, with very small base of near Yellow, Group 8C and shading to light pink towad outer edges of petals; inside surface—Near Red-Purple, Group 58C, with very small base of near Yellow, Group 8C and shading to light pink toward outer edges of petals.

*General color effect.*—Newly opened flower—Light red. 3-days open—Light red, with shades of magneta.

*Behavior.*—Drop off cleanly; persist in hot, dry weather, but hot, dry weather retards blooming cycle.

*Flower longevity.*—On bush in garden—4 or 5 days in August. Cut roses grown outdoors and kept at living-room temperatures—3 or 4 days in August. Cut roses grown in greenhouse and kept at living-room temperatures—4 or 5 days in August.

*Reproductive organs*

Stamens: Average number; arranged irregularly about pistils; a few mixed with petaloids.

Filaments: Medium length; most with anthers.

Anthers: Medium size; all open approximately at once.

*Color*—

*Upper side.*—Near Orange, Group 26B.

*Under side.*—Near Orange, Group 26C.

Pollen: Not observed.

Pistils: Many (approximately 200 in number).

Styles: Uneven; from short to average length; average caliper; somewhat bunched.

Stigma: Color—Near Yellow-Orange, Group 22B.

Ovaries: Usually all enclosed in calyx.

Hips: Average length; flat on top, but generally globular; some seed protruding from top of hip; moderately smooth; walls thin and fleshy. Color—Near Yellow-Orange, Group 22A.

Sepals: Falling soon; from medium length to long; spear-shaped; recurved. Color—

*Inside.*—Near Yellow-Green, Group 146B, with vary-shades of near Red-Purple, Group 59B.

*Outside.*—Near Yellow-Green, Group 146B, with varying shades of near Red-Purple, Group 59B.

Seeds: Few (from 10 to 16 in number); from small to medium size.

*Plant*

Foliage:

*Leaves.*—Compound of usually 3–5 leaflets; abundant; medium size; moderately heavy; somewhat leathery; semiglossy.

*Leaflets.*—Shape — oval — apex — acute — base — round—margin—irregularly serrate.

*Color.*—Mature—upper surface—Near Yellow-Green, Group 147A—under surface—Near Yellow-Green, Group 148B—young— upper surface—Near Yellow-Green, Group 146A—under surface—Near Yellow-Green, Group 146C.

*Rachis (the supporting stem of the compound leaf).*—Average size—upper side—grooved; with some stipitate glands on edges—under side—moderately smooth; with stipitate glands.

*Stipules.*—Medium length; medium width; with points of medium length turning out at an angle of more than 45°.

*Diseases resistance.*—Only mildly subject to mildew, as determined by comparison with other rose varieties grown under comparable conditions at Hemet, Calif., U.S.A.

Growth:

*Habit.*—Bushy; upright; moderately branched.

*Growth.*—Moderately vigorous.

*Canes.*—Medium caliper.

*Main stems.*—Color—Near Yellow-Green, Group 147B. *Large prickles*—several; medium length; almost straight, but bending slightly downward; with narrow base of medium length—color—near Greyed-Orange, Group 165A. *Small prickles*—several—color—near Greyed-Orange, Group 165A. *Hairs*—none.

*Branches.*—Color—Near Yellow-Green, Group 147B. *Large prickles*—many; medium length; almost straight, but bending slightly downward; with moderately narrow base of medium length—color—near Greyed-Orange, Group 165A. *Small prickles*—several—color—near Greyed-Orange, Group 165A. *Hairs*—none.

*New shoots.*—Color—Near Yellow-Green, Group 146B, with shades of near Red-Purple, Group 59B. *Large prickles*—several; medium length; almost straight, but bending slightly downward; with narrow base of medium length—color—near Red-Purple, Group 59D, with tips of near Yellow-Green, Group 152D. *Small prickles* — several. *Hairs*—none.

I claim:

1. A new and distinct variety of rose plant of the hybrid tea class, substantially as herein shown and described, characterized particularly as to novelty by the unique combination of a bushy, upright and vigorous habit of growth, abundant and attractive foliage, a profuse blooming habit, both outdoors and in the greenhouse, high centered flowers of double form and large size, and a distinctive and attractive light red flower color.

No references cited.

ROBERT E. BAGWILL, Primary Examiner